(12) United States Patent
Mawhirt

(10) Patent No.: US 6,221,089 B1
(45) Date of Patent: Apr. 24, 2001

(54) SKIN INCISION DEVICE WITH COMPRESSION SPRING ASSEMBLY

(75) Inventor: James A. Mawhirt, Brooklyn, NY (US)

(73) Assignee: International Technidyne Corporation, Edison, NJ (US)

( * ) Notice: Subject to any disclaimer, the term of this patent is extended or adjusted under 35 U.S.C. 154(b) by 0 days.

(21) Appl. No.: 08/888,502

(22) Filed: Jul. 7, 1997

(51) Int. Cl.[7] ................................................... A61B 17/14
(52) U.S. Cl. ........................ 606/181; 606/182; 606/184; 606/185
(58) Field of Search .................... 606/181, 182, 606/184, 185

(56) References Cited

U.S. PATENT DOCUMENTS

| | | | |
|---|---|---|---|
| 4,136,795 | * | 1/1979 | Crute et al. ............................ 220/203 |
| 4,643,189 | * | 2/1987 | Mintz ..................................... 128/314 |
| 4,766,453 | * | 8/1988 | Shoikama et al. ..................... 354/286 |
| 5,026,223 | * | 6/1991 | Hunt ...................................... 409/233 |
| 5,071,020 | * | 12/1991 | Reutter ................................. 220/203 |
| 5,732,175 | * | 3/1998 | Fan ......................................... 385/87 |

\* cited by examiner

*Primary Examiner*—Michael Buiz
*Assistant Examiner*—Vy Quang Bui
(74) *Attorney, Agent, or Firm*—Arthur L. Plevy

(57) ABSTRACT

A device for making an incision in skin, having a housing with a slotted opening, and a triggering mechanism disposed within the housing for propelling a blade coupled thereto, through the slotted opening of the housing to make an incision in the skin. The triggering mechanism includes a finger engageable trigger located external to the housing for actuating the triggering mechanism and a spring anchoring assembly for automated machine arming the device after the triggering mechanism has been assembled into the housing.

19 Claims, 3 Drawing Sheets

SKIN INCISION DEVICE WITH COMPRESSION SPRING ASSEMBLY

RELATED APPLICATIONS

International Technidyne Corporation, the assignee herein, is record owner of U.S. patent application Ser. No. 08/866,172 entitled ADJUSTABLE SKIN INCISION DEVICE, filed on May 30, 1997, and issuing as U.S. Pat. No. 5,797,940 on Aug. 25, 1998 by Mawhirt et al.

FIELD OF THE INVENTION

The present invention relates to blood drop generation devices for making incisions in skin and more particularly to a blood drop generation device having a compression spring assembly for after assembly access to the blade triggering mechanism.

BACKGROUND OF THE INVENTION

Blood drop generation devices are well known in the art for providing blood samples which are used in performing various blood tests for preventative medicine and medical diagnosis. Such devices operate by creating a small puncture or incision in the skin of the fingertip or other area of the body such as the foot, arm, or leg.

Since most blood drop generation devices employ a lancet-like structure for puncturing or incising the skin, blood drop generation devices are often referred to as lancet devices. Many prior art lancet devices employ spring loaded cutting blades which are enclosed within a casing or housing. These devices are operated by placing the housing of the device against the skin and triggering the spring loaded cutting blade in the device. The potential energy stored within the spring accelerates the blade through an aperture in the housing and creates a uniform puncture or incision in the skin. The structural configuration of these devices enable the puncture or incision in the skin to be made in a controlled manner in terms of location, size, depth, and sterility. Since the blade is concealed within the housing, the patient is unable to view the blade prior to, or during the puncturing of the skin which reduces the patient's anxiety. Further, most recent designs of lancet devices include means for retracting the blade back into the housing after the puncture or incision has been made. Such a safety feature advantageously reduces the probability of a disease being spread through contact with the used blade of the device. This is an important feature since, deadly viruses such as AIDS and Hepatitis can spread from accidental punctures obtained from lancets used previously on an infected patient.

As already mentioned, the structural configuration of a lancet device enables it to puncture or incise the skin in a controlled manner in terms of location, size and depth. Devices which puncture the skin employ cutting blades which plunge perpendicularly into the skin to produce a skin incision of a predetermined depth. Such lancets are exemplified in U.S. Pat. No. 5,133,730 to Biro. In U.S. Pat. No. 5,133,730, a sharp blade is provided on a spring biased pivot arm which moves the blade out through an orifice in the lancet housing and then retracts the blade back into the housing. Although the blade is positioned on a pivot arm, the blade is directed perpendicularly, into the surface of the skin. The shape of the blade helps the blade enter the skin and make the needed incision. Other lancet devices that create plunge-type cuts are described in U.S. Pat. No. 3,760,809 to Cambell, Jr. and U.S. Pat. No. 5,395,388 to Schrage.

Lancet devices which incise the skin employ cutting blades which move in an arcuate motion or cutting blades which move simultaneously in a perpendicular and transverse motion. The lancet devices employing cutting blades that incise the skin in an arcuate manner are exemplified in U.S. Pat. No. 3,902,475 to Berg et al. The lancets in U.S. Pat. No. 3,902,475 produce skin incisions that vary in depth along the length of the incision. Consequently, in order to obtain a requisite incision depth of between 1 and 5 mm, such lancet devices must produce incisions that are relatively long and thus, less desirable.

The lancet devices employing cutting blades that incise the skin in a simultaneous perpendicular and transverse motion are capable of producing skin incisions which are uniform in depth along the entire length of the incision. Such a lancet device is described in U.S. Pat. No. 4,643,189 to Mintz. The simultaneous perpendicular and transverse motion of the cutting blade is accomplished by providing a unique cam configuration which controls the path of a pivoting arm that contains a cutting blade. The cutting blade is powered by a looped straight-arm torsion spring which is installed when the lancet device is assembled.

SUMMARY

A device for making an incision in skin, comprising a housing having a slotted opening and triggering means disposed within the housing for propelling a blade coupled thereto, through the slotted opening of the housing a given distance to make an incision of a predetermined size in the skin. The triggering means includes separate spring biasing means for arming the device after the triggering means have been assembled into the housing.

In another embodiment, the triggering means includes an arm link which couples the blade, the spring biasing means rotating the arm link when the device is activated to propel the blade through the slotted opening of the housing when the device is activated. In a further embodiment, the removable spring biasing means includes a coil spring that engages the arm link.

In still another embodiment, the separate spring biasing means and the housing include bayonet locking means for retaining the separate spring biasing means to the housing after complete assembly of the remaining parts; the housings, the blade holder and the triggering means.

BRIEF DESCRIPTION OF THE DRAWINGS

For a detailed understanding of the present invention, reference should be made to the following detailed description taken in conjunction with the accompanying drawings wherein.

DETAILED DESCRIPTION OF THE INVENTION

Figure 1A:
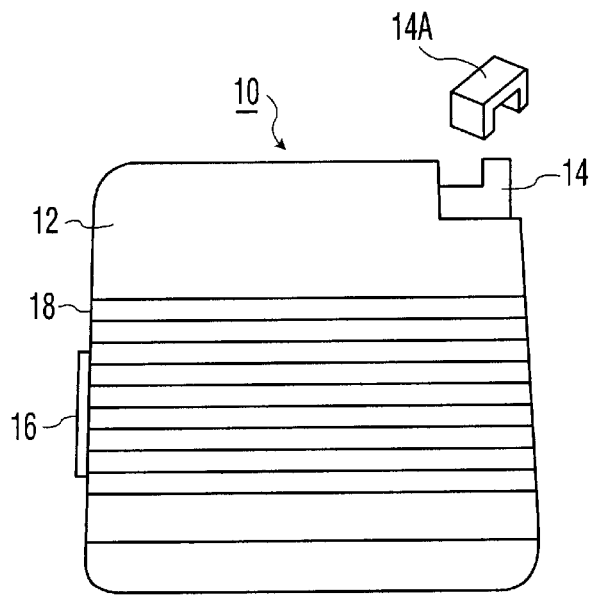
FIG. 1A is an elevational view of a lancet device in accordance with an embodiment of the present invention.

Referring now to FIG. 1A, an elevational view of a lancet device according to an exemplary embodiment of the present invention is shown and denoted by the numeral 10. The lancet device 10 is especially suited for making skin incisions in the heel of newborn infants, however, the lancet device of the present invention is also suited for making skin incisions in toddlers, children and adults. The lancet device 10 is based on the lancet device described in U.S. Pat. No. 4,643,189. Accordingly, the teachings of this patent as they apply to the present invention, are incorporated herein by reference.

Referring still to FIG. 1A, the lancet device 10 comprises a housing 12 molded from any suitable plastic. The housing 12 encloses a blade triggering mechanism that is activated by pushing a trigger 14 as will be explained. The spring anchor head member 16 is located on a first side 18 of the housing 12.

Figure 2A:
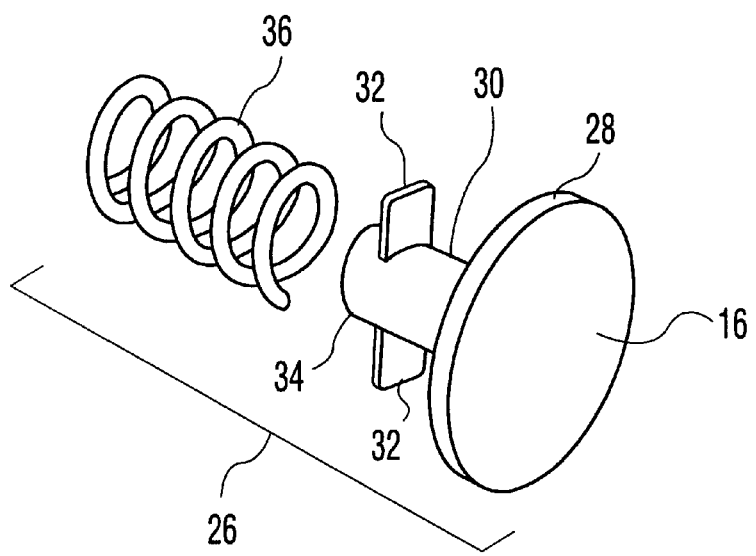
FIG. 2A is an exploded perspective view of an embodiment of the spring anchor assembly.
Figure 2B:
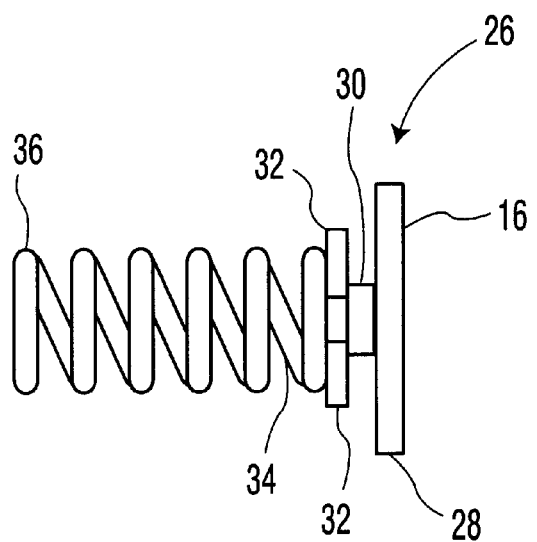
FIG. 2B is a side elevational view of the spring anchor assembly of FIG. 2A.

In FIGS. 2A and 2B, the head member 16 is a component of a spring anchor assembly 26 that is designed to be machine installed within the housing 12 after the lancet device 10 has been assembled with all internal components in the armed position. The spring anchor assembly 26 comprises a dual tab, headed spring anchor 28 and a coil spring 36. The thumb-screw 28 is unitarily formed to include the machine interfacing rotatable head member 16 and a centrally located cylindrical-shaped shaft member 30. A pair of radially extending locking tabs 32 are disposed 180 degrees apart from each other on the shaft 30 at the marginal end thereof. The back sides of the tabs 32 and the end portion 34 of the shaft 30 form spring seat for the compression coil spring 36.

Figure 1B:
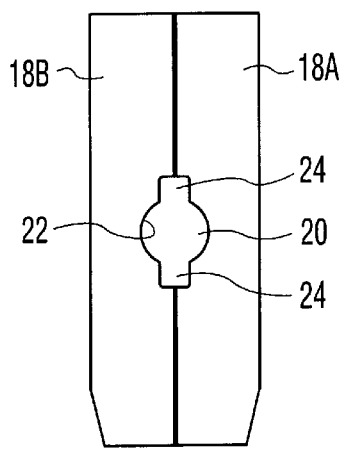
FIG. 1B is a side elevational view of the lancet device of FIG. 1A without a spring and spring anchor assembly installed.
Figure 1C:
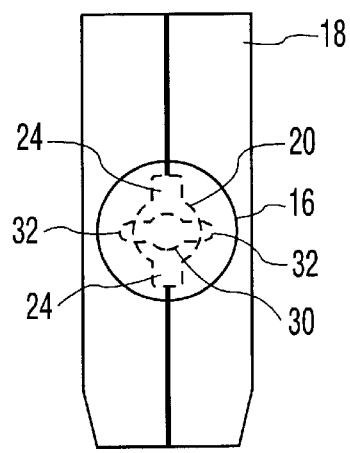
FIG. 1C is a side elevational view of the lancet device of FIG. 1A with the spring and spring anchor assembly installed.

In FIG. 1B, a side view of the lancet device 10 of FIG. 1A, is depicted without the spring anchor assembly 26 installed therein. As can be seen, the side 18A and 18B of the housing 10 includes an installation aperture 20 for removably receiving the spring anchor assembly 26. The aperture 20 is formed half in 18A and 18B. The installation aperture 20 has a circular-shaped opening 22 with a pair of slots 24 disposed 180 degrees apart from each other. The slots 24 of the installation aperture 20 and the locking tabs 32 of the headed spring anchor 28 coact to define a one-quarter turn bayonet-style spring anchor assembly locking arrangement as illustrated in FIG. 1C. The locking tabs 32 engage the recesses of the slots 24 to permanently secure the spring anchor and to further provide separation resistant grips to the housing halves, 18A and 18B.

Figure 3A:
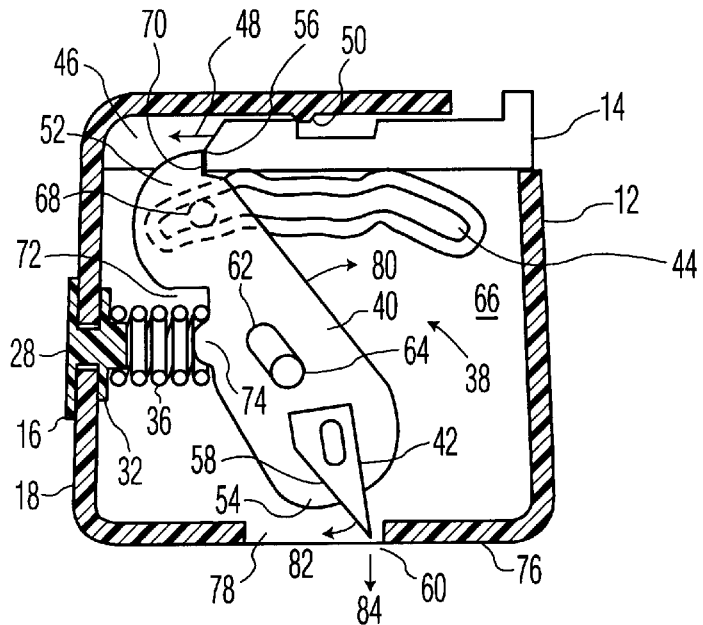
FIG. 3A is a cross-sectional view of the lancet device of FIG. 1A in the armed position prior to activation.

As is visible in the cross-sectional view of FIG. 3A, the spring anchor assembly is one of the components of the earlier mentioned blade triggering mechanism 38. The other major components of the blade triggering mechanism 38 include the trigger 14, the user removable safety 14A, a blade holder/follower 40 which holds a triangular cutting blade 42, and a cam channel 44. The blade triggering mechanism 38 is depicted in FIG. 3A in an armed position after the installation of the spring anchor assembly 26. The trigger 14 is a plunger-like device that is moveable in the direction of arrow 48 in a channel 46 defined by the housing 12. The channel 46 has a projecting boss 50 that holds the trigger 14 in the armed position before activation of the lancet device 10.

The blade holder/follower 40 of the blade triggering mechanism 38 has a detent or notch 56 at a first end 52 thereof. The triangular blade 42 with a cutting edge 58 and sharpened apex 60, is disposed at a second end 54 of the blade holder/follower 40. The blade 42 may be secured to the arm link 40 by any conventional means and is scalpel-like in appearance and function. An elongated slotted opening 78 through which the blade 42 is directed, is provided in the base 76 of the housing 12. The blade holder/follower 40 includes an elongated aperture 62 which allows the blade holder/follower 40 to simultaneously rotate and reciprocate on a pivot shaft 64 defined on an inner surface 66 of the housing 12. The blade holder/follower 40 also includes a cam follower 68 (shown in broken lines) disposed marginally adjacent to the first end 52 thereof. The cam follower 68 follows the specially profiled cam channel 44 defined on the inner surface 66 of the housing 12, which causes the blade holder/follower 40 to simultaneously rotate and reciprocate according to the profile of the cam channel 44 when the device is activated. The detent 56 of the blade holder/follower 40, coacts with the end 70 of the trigger 14 to retain the blade holder/follower 40 in the armed position. The blade holder/follower 40 also includes a notched area 72 with a centrally located protrusion 74 which accommodates and grips the free end of the coil spring 36 of the spring anchor assembly 26, when the spring anchor assembly 26 is installed in the housing 12 to arm the lancet device 10. With the spring anchor assembly 26 installed, the coil spring 36 is compressed between the thumb screw 28 and the locked blade holder/follower 40.

Figure 3B:
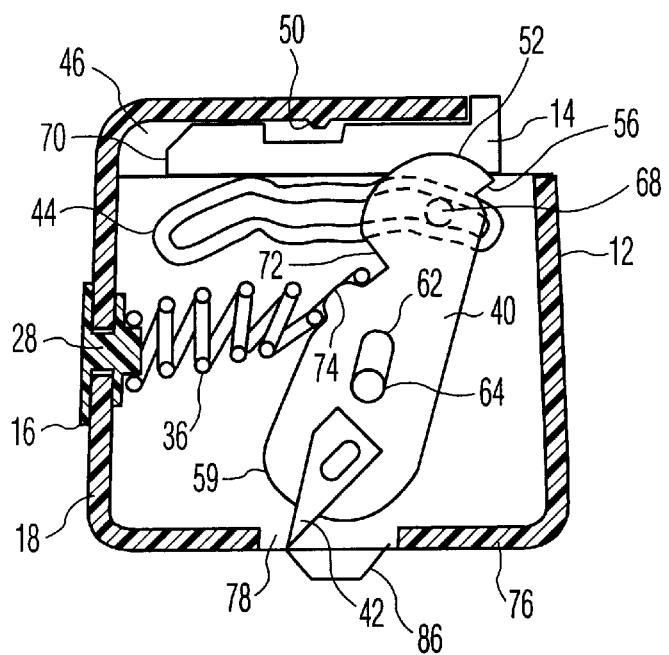
FIG. 3B is a cross-sectional view of the lancet device of FIG. 1A, after the device has been activated.

When the lancet device 10 is activated, the operator removes the safety 14A and pushes the trigger 14 in the direction of the arrow 48 which pushes the first end 52 of the blade holder/follower 40 toward the end wall 18 of the housing 12 until the end 70 of the trigger 14 disengages from the detent in the blade holder/follower 40. At this position, the energy stored in the compressed spring 36 (which is now almost fully compressed) is released and drives and rotates the blade holder/follower 40 in the direction of arrow 80 thus, causing the cutting edge 58 of the blade 42 to move out of the housing 12 through the elongated aperture 78 in the direction indicated by arrows 84, 82, 84A with the arm link's motion being controlled by the profile of the cam channel 44. More specifically, the cam channel 44 causes the blade holder/follower 40 to first rotate in the direction of the arrow 82 and then move linearly in the direction of arrow 84 which causes the apex 60 and cutting edge 58 of the blade 42 to immediately more vertically from the housing 12 through the elongated slot 78 a predetermined distance as determined by the profile of the cam channel 44 to puncture the skin. The vertical motion 84 permits instantaneous full penetration of the incision blade 42. With the cutting edge 58 of the blade 42 in the skin, linear movement in the direction of arrow 84 is virtually halted, and rotation of the arm link 40 continues on for a predetermined number of degrees as controlled by the cam channel 44 which produces an incision of a uniform depth as depicted by the blade cut path 86 shown in FIG. 3B. Then, the profile of the cam channel 44 causes the blade holder/follower 40 to move linearly in the direction of the arrow 84A to vertically withdraw the blade 42 from the skin and back into the housing 12 through the elongated slot 78. The vertical withdrawal eliminates tissue tearing at the end of the incision. The faceted recess 16A is configured to permit automatic insertion and rotation of spring anchor 28 with the spring 36 attached. Features molded into the case 18, sides will guide the spring 36 onto the seating and gripping feature 74 of blade holder/follower 40.

It will be understood that the embodiments described herein are merely exemplary and that a person skilled in the art may make many variations and modifications to the described embodiments utilizing functionally equivalent elements to those described. For example, other embodiments of the thumb screw can include more than two locking tabs with a correspondingly constructed installation aperture in the housing or any other type of well known screw thread arrangement. Any variations or modifications to the invention described hereinabove are intended to be included within the scope of the invention as defined by the appended claims.

What is claimed is:

1. A device for making an incision in skin, comprising:
   a housing having a slotted opening and an aperture;
   triggering means disposed within said housing for propelling a blade coupled thereto, through said slotted opening of said housing a given distance to make an incision of a predetermined size in the skin, said triggering means including removable spring biasing means wherein after assembly of said triggering means in said housing, said spring biasing means engages said housing through said aperture and arms said device.

2. The device according to claim 1, wherein said removable spring biasing means includes automated machine actuable means disposed externally on said housing for manually locking and unlocking said spring biasing means.

3. The device according to claim 1, wherein said triggering means includes an arm link which couples said blade, said spring biasing means rotating said arm link when said device is activated to propel said blade through said slotted opening of said housing when said device is activated.

4. The device according to claim 3, wherein said removable spring biasing means includes a coil spring that engages said arm link of said triggering means.

5. The device according to claim 4, wherein said removable spring biasing means further includes spring anchoring means, said coil spring being compressed between said spring anchoring means and said arm link when said device is armed and rotating said arm link when said device is activated to propel said blade through said slotted opening of said housing.

6. The device according to claim 1, wherein said removable spring biasing means and said housing include bayonet locking means for retaining said spring biasing means to said housing.

7. The device according to claim 6, wherein said bayonet locking means include opposing locking tabs on said removable spring biasing means.

8. The device according to claim 7, wherein said bayonet locking means further include an aperture with a pair of opposing slots for receiving said locking tabs of said removable spring biasing means.

9. The device according to claim 1, wherein said housing has a base which defines said slotted opening.

10. A device for making an incision in skin, comprising;
    a housing having a slotted opening and an aperture;
    triggering means disposed within said housing, for propelling a blade coupled thereto, through said slotted opening of said housing a given distance to make an incision of a predetermined size in the skin, and then retracting said blade through said slotted opening into said housing, said triggering means including a finger engageable trigger located external to said housing for actuating said triggering means, and removable spring biasing means engaging said housing through said aperture and arming said device after said triggering means have been assembled into said housing.

11. The device according to claim 10, wherein said housing includes cam means for causing said blade to produce a cut path of a predetermined length in the skin which is substantially uniform in depth along said predetermined length, the cut path providing an instantaneous full depth cut and an instantaneous vertical pull out at the end of the cut preventing tissue tearing.

12. The device according to claim 10, wherein said triggering means includes a blade holder/follower which couples said blade, said spring biasing means rotating said blade holder/follower when said device is activated to propel said blade through said slotted opening of said housing when said device is activated.

13. The device according to claim 12, wherein said removable spring biasing means includes a coil spring that engages said blade holder/follower.

14. The device according to claim 13, wherein said removable spring biasing means further includes a headed anchor, said coil spring being compressed between said headed anchor and said blade holder/follower when said device is armed and rotating said blade holder/follower when said device is activated to propel said blade through said slotted opening of said housing.

15. The device according to claim 10, wherein said removable spring biasing means and said housing include bayonet locking means for retaining said removable spring biasing means to said housing.

16. The device according to claim 15, wherein said bayonet locking means include opposing locking tabs on said spring biasing means.

17. The device according to claim 16, wherein said bayonet locking means further include an aperture with a pair of opposing slots for receiving said locking tabs of said removable spring biasing means.

18. The device according to claim 10, wherein said housing has a base which defines said slotted opening.

19. The device according to claim 10, wherein said removable spring biasing means include:
    a headed anchor having a pair of opposing locking tabs which pass through a correspondingly shaped aperture in said housing to provide automated machine insertion and locking of said spring biasing means to said housing, and
    a coil spring abutted against said locking tabs, said spring becoming compressed between a blade holder/follower member of said triggering means which couples said blade and said locking tabs of said headed anchor when said removable spring biasing means is installed in said housing to arm said lancet device after assembly.

* * * * *